United States Patent
Chen et al.

(10) Patent No.: US 8,158,440 B2
(45) Date of Patent: Apr. 17, 2012

(54) METHOD FOR QUANTITATIVE MEASUREMENT OF THYROID RELATED ANTIBODIES OR ANTIGENS IN A SERUM SAMPLE

(75) Inventors: Zhong Chen, Sandy, UT (US); Ning Liu, Beijing (CN); Yancun Li, Beijing (CN)

(73) Assignee: CMED Technologies Ltd., Road Town, Tortola (VG)

( * ) Notice: Subject to any disclaimer, the term of this patent is extended or adjusted under 35 U.S.C. 154(b) by 394 days.

(21) Appl. No.: 12/442,381

(22) PCT Filed: Sep. 17, 2007

(86) PCT No.: PCT/US2007/078665
§ 371 (c)(1),
(2), (4) Date: Mar. 20, 2009

(87) PCT Pub. No.: WO2008/067007
PCT Pub. Date: Jun. 5, 2008

(65) Prior Publication Data
US 2009/0280575 A1 Nov. 12, 2009

Related U.S. Application Data

(60) Provisional application No. 60/827,258, filed on Sep. 28, 2006.

(51) Int. Cl.
*G01N 33/53* (2006.01)
*G01N 33/553* (2006.01)

(52) U.S. Cl. .......... 436/500; 385/12; 385/129; 385/130; 422/82.11; 435/287.2; 435/288.7; 435/808; 436/164; 436/525; 436/805; 436/815

(58) Field of Classification Search .......... None
See application file for complete search history.

(56) References Cited

U.S. PATENT DOCUMENTS

| | | |
|---|---|---|
| 4,609,629 A | 9/1986 | Timpl |
| 4,755,458 A | 7/1988 | Rabbani et al. |
| 5,242,828 A | 9/1993 | Bergstrom et al. |
| 5,478,755 A | 12/1995 | Attridge et al. |
| 5,573,957 A | 11/1996 | Cardone et al. |
| 5,629,213 A | 5/1997 | Kornguth et al. |
| 5,712,087 A | 1/1998 | Houghton et al. |
| 5,846,740 A | 12/1998 | Tobin et al. |
| 6,197,515 B1 | 3/2001 | Bamdad et al. |
| 6,468,657 B1 | 10/2002 | Hou et al. |
| 6,534,281 B2 | 3/2003 | Kitajima et al. |
| 6,627,397 B1 | 9/2003 | Nakamura et al. |
| 6,726,881 B2 | 4/2004 | Shinoki et al. |
| 6,809,196 B2 | 10/2004 | Bamdad et al. |
| 6,956,651 B2 | 10/2005 | Lackritz et al. |
| 6,967,074 B2 | 11/2005 | Duffy et al. |
| 7,135,281 B2 | 11/2006 | Doorbar |
| 2003/0032202 A1 | 2/2003 | Stolowitz et al. |
| 2004/0115684 A1 | 6/2004 | Costa |
| 2004/0219523 A1 | 11/2004 | Stanton et al. |
| 2004/0234970 A1 | 11/2004 | Yoo |
| 2005/0019933 A1 | 1/2005 | Andersson et al. |
| 2005/0064450 A1 | 3/2005 | Lucas et al. |
| 2005/0100974 A1 | 5/2005 | Duffy et al. |
| 2005/0106562 A1 | 5/2005 | Abbott et al. |
| 2005/0153357 A1 | 7/2005 | Eichler et al. |
| 2006/0083858 A1 | 4/2006 | Barden et al. |
| 2006/0211137 A1 | 9/2006 | Ezoe et al. |

FOREIGN PATENT DOCUMENTS

| | | |
|---|---|---|
| EP | 1 715 344 | 10/2006 |
| JP | 11242031 | 2/1998 |
| WO | 01/68915 | 9/2001 |
| WO | 2004/081572 | 9/2004 |
| WO | 2005/017122 | 2/2005 |
| WO | 2006/074130 | 7/2006 |

OTHER PUBLICATIONS

Artsaenko et al., Abrogation of hepatitis C virus NS3 helicase enzymatic activity by recombinant human antibodies, Journal of General Virology, 2003, pp. 2323-2332, vol. 84.
Aslan et al., Tunable plasmonic glucose sensing based on the dissociation of Con A-aggregated dextran-coated gold colloids, Analytica Chimica Acta, 2004, pp. 139-144, vol. 517.
Breveglieri et al., Recent advances in molecular diagnosis using surface plastmon resonance and biosensor technology for detection of $-thalassemia mutations, Minerva Biotec, 2003, pp. 93-97, vol. 15.
Campagnolo et al., Real-Time, label-free monitoring of tumor antigen and serum antibody interactions, Journal of Biochemcial and Biophysical Methods, 2004, pp. 283-298, vol. 61.
Cherif et al., Clinically Related Protein-Peptide Interactions Monitored in Real Time on Novel Peptide Chips by Surface Plasmon Resonance Imaging, Clinical Chemistry, 2006, pp. 255-262, vol. 52, No. 2. Choi et al., Enhanced performance of a surface plasmon resonance immunosensor for detecting Ab-GAD antibody based on the modified self-assembled monolayers, Biosensors and Bioelectronics, 2005, pp. 378-383, vol. 21.
Chou et al., Development of an immunosensor for human ferritin, a nonspecific tumor marker, based on surface plasmon resonance, Biosensors and Bioelectronics, 2004, pp. 999-1005, vol. 19.
Engels et al., Comprehensive analysis of human subtelomeres with combined binary ration labelling fluorescence in situ hybridisation, European Journal of Human Genetics, 2003, pp. 643-651, vol. 11.
Hagedorn et al., Evaluation of INNO-LIA Syphilis Assay as a Confirmatory Test for Syphilis, Journal of Clinical Microbiology, Mar. 2002, pp. 973-978, vol. 40, No. 3.
Halling et al., Clinical Comparison of the Treponema pallidum CAPTIA Syphilis-G Enzyme Immunoassay with the Fluorescent Treponemal Antibody Absorption Immunoglobulin G Assay for Syphilis Testing, Journal of Clinical Microbiology, Oct. 1999, pp. 3233-3234, vol. 37, No. 10.

(Continued)

*Primary Examiner* — Chris L Chin
(74) *Attorney, Agent, or Firm* — Clayton, Howarth & Cannon, P.C.

(57) ABSTRACT

This invention discloses using SPR technology to simultaneously and quantitatively measure the concentrations of thyroid hormones and related antibodies in a serum sample, which can be used to evaluate thyroid functions and to diagnose thyroid diseases. It also discloses an efficient formula to make a mixed SAM that can greatly enhance the immobilization ability of the metal surface in SPR based techniques, which is good for the immobilization of relevant antibodies and antigens used for the detection of respective thyroid hormones and related antibodies in a serum sample.

14 Claims, No Drawings

OTHER PUBLICATIONS

Hifumi et al., Eliminiation of Ingredients Effect to Improve the Detection of Anti HIV-1 p24 Antibody in Human Serum Using SPR Apparatus, Analytical Sciences, Aug. 2002, pp. 863-867, vol. 18.

Koga et al., A chip-based miniaturized format for protein-expression profiling: The exploitation of comprehensively produced antibodies, Electrophoresis, 2006, pp. 3676-3683, vol. 27.

Lee J. et al., Characterization of a self-assembled monolayer of thiol on a gold surface and the fabrication of a biosensor chip based on surface plasmon resonance for detecting anti-GAD antibody, Biosensors and Bioelectronics, 2005, pp. 1422-1427, vol. 20.

Lee, W. et al., Fabrication of self-assembled protein A monolayer and its application as an immunosensor, Biosensors and Bioelectronics, 2003, pp. 185-192, vol. 19.

Löfös, Dextran modified self-assembled monolayer surfaces for use in biointeraction analysis with surface plasmon resonance, Pure & Applied Chem., 1995, pp. 829-834, vol. 67, No. 5.

McGill et al., Analysis of the binding of monoclonal and polyclonal antibodies to the glycoproteins of antigenic variants of human respiratory syncytial virus by surface plasmon resonance, Journal of Immunological Methods, 2005, pp. 143-152, vol. 297.

Metzger et al., Biosensor Analysis of $2-Glycoprotein I-Reactive Autoantibodies: Evidence for Isotype-Specific Binding and Differentiation of Pathogenic from Infection-Induced Antibodies, Clinical Chemistry, 2007, pp. 11347-11143, vol. 53, No. 6.

Mullet et al., "Surface Plasmon Resonance-Based Immunoassays," Methods, 2000, pp. 77-91, vol. 22.

Nanoprobes E-News, "Gold Particles for Surface Plasmon Resonance Detection," 2004, p. 5, para. 1-3, vol. 5, No. 6.

Soroka et al., "Modification of Rapid Human Immunodeficiency Virus (HIV) Antibody Assay Protocols for Detecting Recent HIV Seroconversion," Clinical and Diagnostic Laboratory Immunology, Aug. 2005, pp. 918-921, vol. 12, No. 8.

Stock et al., "Migration of human melanoma cells depends on extracellular pH and Na+/H+ exchance," J Physiol, 2005, pp. 225-238, vol. 567.1.

Subramanian et al., "A mixed self-assembled monolayer-based surface plasmon immunosensor for detection of E. coli O157:H7," Biosensors and Bioelectronics, 2006, pp. 998-1006, vol. 21.

Tong et al., "Diagnostic developments involving cell-free (circulating) nucleic acids," Clinica Chimica Acta, 2006, pp. 187-196, vol. 363.

Urban et al., "Receptor recognition by a hepatitis B virus reveals a novel mode of high affinity virus-receptor interaction," The EMBO Journal, 2000, pp. 1217-1227, vol. 19, No. 6.

Vaisocherova et al., SPR Biosensors for Medical Diagnostics, Springer Series on Chemical Sensors and Biosensors, 2006, pp. 229-247, vol. 4, part III.

Wang et al., "A new approach for the detection of DNA sequences in amplified nucleic acids by a surface plasmon resonance biosensor," Biosensors and Bioelectronics, 2004, pp. 598-605, vol. 20.

Wu et al., "Study of MMLV RT-Binding with DNA using Surface Plasmon Resonance Biosensor," Acta Biochimica et Biophysica Sinica, 2005, pp. 634-642, vol. 37, No. 9.

METHOD FOR QUANTITATIVE MEASUREMENT OF THYROID RELATED ANTIBODIES OR ANTIGENS IN A SERUM SAMPLE

CROSS-REFERENCE TO RELATED APPLICATIONS

This application claims priority benefits under 35 U.S.C. 365(a) of International Application No. PCT/US07/78665, filed 17 Sep. 2007, which claims priority under the Paris Convention to U.S. Provisional Patent Application No. 60/827,258, filed on 28 Sep. 2006, which applications are incorporated by reference herein in their entireties, including but not limited to those portions that specifically appear hereinafter.

TECHNICAL FIELD

The present invention relates to a method of using SPR technology to simultaneously detect the levels of thyroid hormones and related antibodies in a serum sample.

INDUSTRIAL APPLICABILITY

It has been recognized that it would be advantageous to develop a label-free and high-throughput technique to detect the levels of thyroid hormones and related antibodies in a serum sample. The METHOD FOR THE QUANTITATIVE MEASUREMENT OF THYROID HORMONES AND RELATED ANTIBODIES IN A SERUM SAMPLE relates to a novel method of using SPR technology to quantitatively measure the concentrations of different thyroid hormones and related antibodies, which can be used to evaluate thyroid functions and to diagnose thyroid disorders. The METHOD FOR THE QUANTITATIVE MEASUREMENT OF THYROID HORMONES AND RELATED ANTIBODIES IN A SERUM SAMPLE provides an efficient formula to make a mixed SAM in and a method of using thereof for the immobilization of relevant antibodies and antigens in a SPR system for the quantitative evaluation of thyroid hormones and related antibodies in a serum sample.

DISCLOSURE OF THE INVENTION

Surface plasmon resonance (SPR) technology has been employed for quantitative and qualitative analysis in analytical chemistry, biochemistry, physics and engineering. SPR technology has become a leading technology in the field of direct real-time observation of biomolecular interactions.

SPR technology is highly sensitive to changes that occur at the interface between a metal and a dielectric medium (e.g., water, air, etc). In general, a high-throughput SPR instrument consists of an auto-sampling robot, a high resolution CCD (charge-coupled device) camera, and gold or silver-coated glass slide chips each with more than 4 array cells embedded in a plastic support platform.

SPR technology exploits surface plasmons (special electromagnetic waves) that can be excited at certain metal interfaces, most notably silver and gold. When incident light is coupled with the metal interface at angles greater than the critical angle, the reflected light exhibits a sharp attenuation (SPR minimum) in reflectivity owing to the resonant transfer of energy from the incident light to a surface plasmon. The incident angle (or wavelength) at which the resonance occurs is highly dependent upon the refractive index in the immediate vicinity of the metal surface. Binding of biomolecules at the surface changes the local refractive index and results in a shift of the SPR minimum. By monitoring changes in the SPR signal, it is possible to measure binding activities at the surface in real time. Traditional SPR spectroscopy sensors, which measure the entire SPR curve as a function of angle or wavelength, have been widely used, but offer limited throughput. The high-throughput capability of a high-throughput SPR instrument is largely due to its imaging system. The development of SPR imaging allows for the simultaneous measurement of thousands of biomolecule interactions.

Typically, a SPR imaging apparatus consists of a coherent p-polarized light source expanded with a beam expander and consequently reflected from a SPR active medium to a detector. A CCD camera collects the reflected light intensity in an image. SPR imaging measurements are performed at a fixed angle of incidence that falls within a linear region of the SPR dip; changes in light intensity are proportional to the changes in the refractive index caused by binding of biomolecules to the surface. As a result, gray-level intensity correlates with the amount of material bound to the sensing region. In addition, one of the factors determining the sensitivity of a SPR imaging system is the intensity of the light source. The signal strength from the metal surface is linearly proportional to the incoming light strength, so a laser light source is preferred over light-emitting diode and halogen lamps.

The SPR instrument is an optical biosensor that measures binding events of biomolecules at a metal surface by detecting changes in the local refractive index. The depth probed at the metal-aqueous interface is typically 200 nm, making SPR a surface-sensitive technique ideal for studying interactions between immobilized biomolecules and a solution-phase analyte. SPR technology offers several advantages over conventional techniques, such as fluorescence or ELISA (enzyme-linked immunosorbent assay) based approaches. First, because SPR measurements are based on refractive index changes, detection of an analyte is label free and direct. The analyte does not require any special characteristics or labels (radioactive or fluorescent) and can be detected directly, without the need for multistep detection protocols. Secondly, the measurements can be performed in real time, allowing the user to collect kinetic data, as well as thermodynamic data. Lastly, SPR is a versatile technique, capable of detecting analytes over a wide range of molecular weights and binding affinities. Therefore, SPR technology is a powerful tool for studying biomolecule interactions. So far, in a research setting, SPR based techniques have been used to investigate protein-peptide interactions, cellular ligation, protein-DNA interactions, and DNA hybridization. However, SPR based approaches have not yet been explored in clinical medicine, especially in clinical laboratory medicine.

Human thyrotropin (thyroid stimulating hormone—hTSH) is a glycoprotein hormone synthesized in and secreted from the thyroid lobe of the pituitary gland. It stimulates the production of thyroid hormones by the thyroid gland. The primary function of hTSH is to regulate the synthesis and secretion of the major thyroid hormones, thyroxin ($T_4$) and 3,3',5'-triiodo-L-thyronine ($T_3$). The level of hTSH is regulated by two major opposing factors. The hTSH-releasing hormone (TRH), a tripeptide produced by the hypothalamus, acts upon the thyrotropes to stimulate the synthesis and secretion of hTSH. The thyroid hormones themselves act by decreasing the responsiveness of the thyrotropes to TRH.

When thyroid hormone levels drop below the normal ranges, the pituitary secretes hTSH, which causes the thyroid gland to produce and release more thyroid hormones. Conversely, when thyroid hormones rise above the normal levels, the pituitary decreases its output of hTSH and the thyroid gland decrease production and secretion of thyroid hormones.

The hTSH from pituitary gland regulates the release of $T_3$ and $T_4$ from the thyroid gland. The thyroid hormones inhibit hTSH secretion by feedback through the hypothalamus. There is also an auto-regulatory mechanism, which ensures that the thyroid hormone pool within the thyroid gland remains constant regardless of fluctuations in the iodine content of the gland. Most of the $T_3$ in blood is associated with carrier proteins; about 80% is non-covalently bound to thyroxin binding globulin (TBG), the rest to thyroxin binding prealbumin (TBPA) and albumin; about 0.3% is found as free hormone in equilibrium with the bound fraction. It has been proposed that only the free hormone fraction is metabolically active.

Thyroglobulin is produced only by the thyroid gland and is a major component of the thyroid follicular colloid. The thyroid hormones, $T_4$ and $T_3$, are synthesized from thyroglobulin. Autoantibodies to thyroglobulin (TG autoantibodies, i.e., anti-TG)) are often present in patients with autoimmune thyroid diseases. Approximate 10% of healthy individuals have low levels of TG autoantibodies; higher concentrations are found in 30% and 85% of patients with Graves' disease and Hashimoto's thyroiditis, respectively. However, elevated levels of antibodies to thyroid peroxidase (TPO autoantibodies, i.e., anti-TPO) occur more frequently than high anti-TG levels in these diseases. The measurements of TG autoantibodies are most useful for the evaluation of samples submitted for thyroglobulin measurements because TG autoantibodies can interfere with both competitive immunoassays and immunometric assays for thyroglobulin.

Anti-TPO antibodies are autoantibodies directed against the TPO enzyme. This enzyme catalyzes the iodination of tyrosine in thyroglobulin during the biosynthesis of $T_3$ and $T_4$. Historically, these antibodies are referred to as antimicrosomal antibodies (AMA) because these antibodies bind to the microsomal part of the thyroid cells. Recent research has identified TPO as the primary antigenic component of microsomes. Thyroid autoimmune disease is the major factor underlying hypothyroidism and hyperthyroidism and tends to occur in a genetically predisposed population. The major thyroid autoimmune diseases are: Hashimoto's thyroiditis and Graves' disease. In virtually all cases of Hashimoto's disease and in the majority of cases of Graves' disease, TPO autoantibodies are elevated. High levels of TPO autoantibodies, in the context of the clinical presentation of hypothyroidism, confirm the diagnosis of Hashimoto's disease.

Clinically, TSH, $T_3$, $T_4$, $FT_3$, $FT_4$, anti-TG and anti-TPO have been used to evaluate thyroid functions and to diagnose thyroid diseases. Traditionally, these parameters are detected by using fluorescent label and/or chemiluminescence-based techniques that may be procedure-tedious and less accurate in quantification. In addition, fluorescent label and chemiluminescence-based techniques cannot detect all the parameters simultaneously. SPR technology has the ability of providing unlabel, high-throughput, and on-line parallel analysis. The present invention demonstrates that SPR technology can be used as a powerful tool to detect the levels of thyroid hormones and related antibodies in a serum sample.

REFERENCES

Mullett W M, Lai E P, Yeung J M. Surface plasmon resonance-based immunoassays. Methods. 2000 September; 22(1):77-91.

Cao C, Kim J P, Kim B W, Chae H, Yoon H C, Yang S S, Sim S J. A strategy for sensitivity and specificity enhancements in prostate specific antigen-alpha1-antichymotrypsin detection based on surface plasmon resonance. Biosens Bioelectron. 2006 May 15; 21(11):2106-13.

Choi S H, Lee J W, Sim S J. Enhanced performance of a surface plasmon resonance immunosensor for detecting Ab-GAD antibody based on the modified self-assembled monolayers. Biosens Bioelectron. 2005 Aug. 15; 21(2): 378-83.

Lee, J. W., Cho, S. M., Sim, S. J., Lee, J., 2005. Characterization of self assembled monolayer of thiol on a gold surface and the fabrication of a biosensor chip based on surface plasmon resonance for detecting anti-GAD antibody. Biosens. Bioelectron. 20, 1422-1427.

Nedelkov D, Nelson R W. Surface plasmon resonance mass spectrometry: recent progress and outlooks. Trends Biotechnol. 2003 July; 21(7):301-5. Review.

Kricka L J, Ji X Y. Supersensitive enzyme immunoassay for thyroid stimulating hormone using a new synergistic enhanced chemiluminescent endpoint. J Biolumin Chemilumin, 1996, 11:137-147.

Bibijana C, Boris C, Roby K, et al. Effect of oxygen abstraction on the peroxidase-luminol-perborate system: relevance to the HRP enhanced chemiluminescence mechanism. J Boilumin Chemilumin, 1994, 9:273-277.

Taimela E, Tahtela R, Koskinen P, et al. Ability of two new thyrotropin (TSH) assays to separate hyperthyroid patients from euthyroid patients with low TSH. Clin Chem, 1994, 40:101-105.

John R, Henley R, David C, et al. Enhanced luminescence immunoassay: evaluation of a new more sensitive thyrotropin assay. Clin Chem, 1986, 32:2178-2183.

Spencer C A, Schwarzbein D, Guttler R B, et al. Thyrotropin (TSH)-releasing hormone stimulation test responses employing third and fourth generation TSH assay. J Clin Endocrinol Metab, 1993, 76:494-498.

Spencer C A, Eigen A, Shen D, et al. Specificity of sensitive assays of thyrotropin (TSH) used to screen for thyroid disease in hospitalized patients. Clin Chem, 1987, 33:1391-1396.

Wilkin Son E, Rae P W H, Thomson K J T, et al. Chemiluminescent third generation assay (Amerlite TSH-30) of thyroid-stimulating hormone in serum or plasma assessed. Clin Chem, 1993, 39:2166-2173.

Ross D S, Daniels G H, Gouveia D. The use and limitations of a chemiluminescent thyrotropin assay as a single thyroid function test in an out-patient endocrine clinic. J Clin Endocrinol Metab, 1990, 71:764-769.

Nicoloff J T, Spencer C A. The use and misuse of the sensitive thyrotropin assays. J Clin Endocrinol Metab, 1990, 71:553-558.

MODES FOR CARRYING OUT THE INVENTION

Before the present method of using SPR technology to simultaneously detect the levels of thyroid hormones and related antibodies in a serum sample is disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference "a thyroid hormone" includes reference to two or more such thyroid hormones.

In describing and claiming the present invention, the following terminology will be used in accordance with the definitions set out below.

"Proteins" and "peptides" are well-known terms in the art, and are not precisely defined in the art in terms of the number of amino acids that each includes. As used herein, these terms are given their ordinary meaning in the art. Generally, peptides are amino acid sequences of less than about 100 amino acids in length, but can include sequences of up to 300 amino acids. Proteins generally are considered to be molecules of at least 100 amino acids.

As used herein, a "metal binding tag" refers to a group of molecules that can become fastened to a metal that is coordinated by a chelate. Suitable groups of such molecules include amino acid sequences including, but not limited to, histidines and cysteines ("polyamino acid tags"). Metal binding tags include histidine tags, defined below.

"Signaling entity" means an entity that is capable of indicating its existence in a particular sample or at a particular location. Signaling entities of the invention can be those that are identifiable by the unaided human eye, those that may be invisible in isolation but may be detectable by the unaided human eye if in sufficient quantity (e.g., colloid particles), entities that absorb or emit electromagnetic radiation at a level or within a wavelength range such that they can be readily determined visibly (unaided or with a microscope including an electron microscope or the like), or spectroscopically, entities that can be determined electronically or electrochemically, such as redox-active molecules exhibiting a characteristic oxidation/reduction pattern upon exposure to appropriate activation energy ("electronic signaling entities"), or the like. Examples include dyes, pigments, electroactive molecules such as redox-active molecules, fluorescent moieties (including, by definition, phosphorescent moieties), up-regulating phosphors, chemiluminescent entities, electrochemiluminescent entities, or enzyme-linked signaling moieties including horse radish peroxidase and alkaline phosphatase.

"Precursors of signaling entities" are entities that by themselves may not have signaling capability but, upon chemical, electrochemical, electrical, magnetic, or physical interaction with another species, become signaling entities. An example includes a chromophore having the ability to emit radiation within a particular, detectable wavelength only upon chemical interaction with another molecule. Precursors of signaling entities are distinguishable from, but are included within the definition of, "signaling entities" as used herein.

As used herein, "fastened to or adapted to be fastened", in the context of a species relative to another species or to a surface of an article, means that the species is chemically or biochemically linked via covalent attachment, attachment via specific biological binding (e.g., biotin/streptavidin), coordinative bonding such as chelate/metal binding, or the like. For example, "fastened" in this context includes multiple chemical linkages, multiple chemical/biological linkages, etc., including, but not limited to, a binding species such as a peptide synthesized on a polystyrene bead, a binding species specifically biologically coupled to an antibody which is bound to a protein such as protein A, which is covalently attached to a bead, a binding species that forms a part (via genetic engineering) of a molecule such as GST or Phage, which in turn is specifically biologically bound to a binding partner covalently fastened to a surface (e.g., glutathione in the case of GST), etc. As another example, a moiety covalently linked to a thiol is adapted to be fastened to a gold surface since thiols bind gold covalently. Similarly, a species carrying a metal binding tag is adapted to be fastened to a surface that carries a molecule covalently attached to the surface (such as thiol/gold binding) and which molecule also presents a chelate coordinating a metal. A species also is adapted to be fastened to a surface if that surface carries a particular nucleotide sequence, and the species includes a complementary nucleotide sequence.

"Covalently fastened" means fastened via nothing other than by one or more covalent bonds. E.g. a species that is covalently coupled, via EDC/NHS chemistry, to a carboxylate-presenting alkyl thiol which is in turn fastened to a gold surface, is covalently fastened to that surface.

"Specifically fastened (or bound)" or "adapted to be specifically fastened (or bound)" means a species is chemically or biochemically linked to another specimen or to a surface as described above with respect to the definition of "fastened to or adapted to be fastened", but excluding all non-specific binding.

"Non-specific binding", as used herein, is given its ordinary meaning in the field of biochemistry.

As used herein, a component that is "immobilized relative to" another component either is fastened to the other component or is indirectly fastened to the other component, e.g., by being fastened to a third component to which the other component also is fastened, or otherwise is translationally associated with the other component. For example, a signaling entity is immobilized with respect to a binding species if the signaling entity is fastened to the binding species, is fastened to a colloid particle to which the binding species is fastened, is fastened to a dendrimer or polymer to which the binding species is fastened, etc. A colloid particle is immobilized relative to another colloid particle if a species fastened to the surface of the first colloid particle attaches to an entity, and a species on the surface of the second colloid particle attaches to the same entity, where the entity can be a single entity, a complex entity of multiple species, a cell, another particle, etc.

The term "sample" refers to any medium suspected of containing an analyte, such as a binding partner, the presence or quantity of which is desirably determined. The sample can be a biological sample such as a cell, cell lysate, tissue, serum, blood or other fluid from a biological source, a biochemical sample such as products from a cDNA library, an environmental sample such as a soil extract, or any other medium, biological or non-biological, including synthetic material, that can advantageously be evaluated in accordance with the invention.

A "sample suspected of containing" a particular component means a sample with respect to which the content of the component is unknown. The sample may be unknown to contain the particular component, or may be known to contain the particular component but in an unknown quantity.

As used herein, a "metal binding tag" refers to a group of molecules that can become fastened to a metal that is coordinated by a chelate. Suitable groups of such molecules include amino acid sequences, typically from about 2 to about 10 amino acid residues. These include, but are not limited to, histidines and cysteines ("polyamino acid tags"). Such binding tags, when they include histidine, can be referred to as a "poly-histidine tract" or "histidine tag" or "HIS-tag", and can be present at either the amino- or carboxy-terminus, or at any exposed region of a peptide or protein or nucleic acid. A poly-histidine tract of six to ten residues is preferred for use in the invention. The poly-histidine tract is also defined functionally as being the number of consecutive histidine residues added to a protein of interest which allows for the affinity purification of the resulting protein on a metal chelate column, or the identification of a protein terminus through interaction with another molecule (e.g. an antibody reactive with the HIS-tag).

A "moiety that can coordinate a metal", as used herein, means any molecule that can occupy at least two coordination sites on a metal atom, such as a metal binding tag or a chelate.

"Affinity tag" is given its ordinary meaning in the art. Affinity tags include, for example, metal binding tags, GST (in GST/glutathione binding clip), and streptavidin (in biotin/streptavidin binding). At various locations herein specific affinity tags are described in connection with binding interactions. It is to be understood that the invention involves, in any embodiment employing an affinity tag, a series of individual embodiments each involving selection of any of the affinity tags described herein.

The term "self-assembled monolayer" (SAM) refers to a relatively ordered assembly of molecules spontaneously chemisorbed on a surface, in which the molecules are oriented approximately parallel to each other and roughly perpendicular to the surface. Each of the molecules includes a functional group that adheres to the surface, and a portion that interacts with neighboring molecules in the monolayer to form the relatively ordered array. See Laibinis. P. E.; Hickman. J.: Wrighton. M. S.: Whitesides, G. M. Science 245, 845 (1989). Bain. C.; Evall. J.: Whitesides. G. M. J. Am. Chem. Soc. 111, 7155-7164 (1989), Bain, C.; Whitesides, G. M. J. Am. Chem. Soc. 111, 7164-7175 (1989), each of which is incorporated herein by reference. The SAM can be made up completely of SAM-forming species that form close-packed SAMs at surfaces, or these species in combination with molecular wires or other species able to promote electronic communication through the SAM (including defect-promoting species able to participate in a SAM), or other species able to participate in a SAM, and any combination of these. Preferably, all of the species that participate in the SAM include a functionality that binds, optionally covalently, to the surface, such as a thiol which will bind covalently to a gold surface. A self-assembled monolayer on a surface, in accordance with the invention, can be comprised of a mixture of species (e.g. thiol species when gold is the surface) that can present (expose) essentially any chemical or biological functionality. For example, they can include tri-ethylene glycol-terminated species (e.g. tri-ethylene glycol-terminated thiols) to resist non-specific adsorption, and other species (e.g. thiols) terminating in a binding partner of an affinity tag, e.g. terminating in a chelate that can coordinate a metal such as nitrilotriacetic acid which, when in complex with nickel atoms, captures a metal binding tagged-species such as a histidine-tagged binding species.

"Molecular wires" as used herein, means wires that enhance the ability of a fluid encountering a SAM-coated electrode to communicate electrically with the electrode. This includes conductive molecules or, as mentioned above and exemplified more fully below, molecules that can cause defects in the SAM allowing communication with the electrode. A non-limiting list of additional molecular wires includes 2-mercaptopyridine, 2-mercaptobenzothiazole, dithiothreitol, 1,2-benzenedithiol, 1,2-benzenedimethanethiol, benzene-ethanethiol, and 2-mercaptoethylether. Conductivity of a monolayer can also be enhanced by the addition of molecules that promote conductivity in the plane of the electrode. Conducting SAMs can be composed of, but are not limited to: 1) poly (ethynylphenyl) chains terminated with a sulfur; 2) an alkyl thiol terminated with a benzene ring; 3) an alkyl thiol terminated with a DNA base; 4) any sulfur terminated species that packs poorly into a monolayer; 5) all of the above plus or minus alkyl thiol spacer molecules terminated with either ethylene glycol units or methyl groups to inhibit non specific adsorption. Thiols are described because of their affinity for gold in ready formation of a SAM. Other molecules can be substituted for thiols as known in the art from U.S. Pat. No. 5,620,820, and other references. Molecular wires typically, because of their bulk or other conformation, create defects in an otherwise relatively tightly-packed SAM to prevent the SAM from tightly sealing the surface against fluids to which it is exposed. The molecular wire causes disruption of the tightly-packed self-assembled structure, thereby defining defects that allow fluid to which the surface is exposed to communicate electrically with the surface. In this context, the fluid communicates electrically with the surface by contacting the surface or coming in close enough proximity to the surface that electronic communication via tunneling or the like can occur.

The term "biological binding" refers to the interaction between a corresponding pair of molecules that exhibit mutual affinity or binding capacity, typically specific or non-specific binding or interaction, including biochemical, physiological, and/or pharmaceutical interactions. Biological binding defines a type of interaction that occurs between pairs of molecules including proteins, nucleic acids, glycoproteins, carbohydrates, hormones and the like. Specific examples include antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, protein/nucleic acid repressor/inducer, ligand/cell surface receptor, virus/ligand, etc.

The term "binding" or "bound" refers to the interaction between a corresponding pair of molecules that exhibit mutual affinity or binding capacity, typically specific or non-specific binding or interaction, including biochemical, physiological, and/or pharmaceutical interactions. Biological binding defines a type of interaction that occurs between pairs of molecules including proteins, nucleic acids, glycoproteins, carbohydrates, hormones and the like. Specific examples include antibody/antigen, anti body/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, protein/nucleic acid repressor/inducer, ligand/cell surface receptor, virus/ligand, etc.

The term "binding partner" refers to a molecule that can undergo binding with a particular molecule. Biological binding partners are examples. For example, Protein A is a binding partner of the biological molecule IgG, and vice versa.

The term "determining" refers to quantitative or qualitative analysis of a species via, for example, spectroscopy, ellipsometry, piezoelectric measurement, immunoassay, electrochemical measurement, and the like. "Determining" also means detecting or quantifying interaction between species, e.g. detection of binding between two species.

The term "self-assembled mixed monolayer" refers to a heterogeneous self-assembled monolayer, that is, one made up of a relatively ordered assembly of at least two different molecules.

"Synthetic molecule", means a molecule that is not naturally occurring, rather, one synthesized under the direction of human or human-created or human-directed control.

The present invention generally relates to a method of using SPR technology to detect thyroid hormones and related antibodies. More specifically, the present invention relates to using SPR technology to quantitatively measure the concentrations of thyroid hormones and related antibodies in a serum sample, which can be used to evaluate thyroid functions and to diagnose thyroid diseases. In addition, the present invention provides an efficient formula to make a mixed SAM that can greatly enhance the immobilization ability of the metal surface, which is desirable for the immobilization of relevant antibodies and antigens for the detection. For the quantitative evaluation of thyroid hormones and related antibodies in a serum sample, the representative antibodies and antigens used to detect the respective thyroid hormones and related antibodies can be selected from the group consisting of the antibodies to TSH, $T_3$, $T_4$, $FT_3$, and $FT_4$ as well as the antigens of anti-TG and anti-TPO.

To enhance the sensitivity and specificity of the SPR immunoassay, a link layer is attached onto the gold film on the surface of a glass chip which serves as a functional structure for further modification of the gold film surface. So far, several immobilization chemistries are suitable for the formation of the link layer, including alkanethiols, hydrogel, silanes, polymer films and polypeptides. Moreover, there are several methods to attach the link layer onto the thin gold surface, such as the Langmuir-Blodgett film method and the self-assembled monolayer (SAM) approach.

The following examples will enable those skilled in the art to more clearly understand how to practice the present invention. It is to be understood that, while the invention has been described in conjunction with the preferred specific embodiments thereof, that which follows is intended to illustrate and not limit the scope of the invention. Other aspects of the invention will be apparent to those skilled in the art to which the invention pertains.

Example 1

Quantitative Detection of Thyroid Hormones and Related Antibodies to Evaluate Thyroid Functions and to Diagnose Thyroid Disorders (A) Testing sample: serum (about 2 ml)
(B) Representative antibodies and antigens used to detect respective thyroid hormones and related antibodies: antibodies to TSH, T3, $T_4$, $FT_3$, and $FT_4$ as well as antigens of anti-TG and anti-TPO, etc.
(C) Procedure:
Step One: Formation of a Linking Layer on the Surface of a Gold-Film Glass Chip:
1. Cleanliness of Substrate
Metal substrates (copper, silver, aluminum or gold) were firstly cleaned with strong oxidizing chemicals ("piranha" solution—$H_2SO_4$:$H_2O_2$) or argon plasmas, then the surfaces of these substrates were washed with ultra pure water and degassed ethanol. After rinsing, the substrates were dried with pure $N_2$ gas stream.
2. Preparation of Self-Assembled Monolayers (SAMs)
Single-component or mixed self-assembled monolayers (SAMs) of organosulfur compounds (thiols, disulfides, sulfides) on the clean metal substrate have been widely applied for chemical modification to develop chemical and biological sensor chips.

Preparing SAMs on metal substrates was achieved by immersion of a clean substrate into a dilute (~1-10 m M) ethanolic solution of organosulfur compounds for 12-18 h at room temperature.

Monolayers comprising a well-defined mixture of molecular structures are called "mixed" SAMs. There are three methods for synthesizing mixed SAMs: (1) coadsorption from solutions containing mixtures of alkanethiols ($HS(CH_2)_nR$+$HS(CH_2)_nR'$), (2) adsorption of asymmetric dialkyl disulfides ($R(CH_2)_mS$—$S(CH_2)_nR'$), and (3) adsorption of asymmetric dialkylsulfides ($R(CH_2)_mS(CH_2)_nR'$), where n and m are the number of methylene units (range from 3 to 21) and R represents the end group of the alkyl chain (—$CH_3$, —OH, —COOH, $NH_2$) active for covalently binding ligands or biocompatible substance. Mixed SAMs are useful for decreasing the steric hindrance of interfacial reaction that, in turn, is useful for studying the properties and biology of cells.

3. Modifying SAMs

Methods for modifying SAMs after their formation are critical for the development of surfaces that present the large, complex ligands and molecules needed for biology and biochemistry. There are two important techniques for modifying SAMs:

(1) Direct Reactions with Exposed Functional Groups
Under appropriate reaction conditions, terminal functional groups (—OH, —COOH) exposed on the surface of a SAM immersed in a solution of ligands can react directly with the molecules present in solution. Many direct immobilization techniques have been adapted from methods for immobilizing DNA, polypeptides, and proteins on SAMs.

(2) Activation of Surfaces for Reactions
An operationally different approach to the functionalization of the surfaces of SAMs is to form a reactive intermediate, which is then coupled to a ligand. In this invention, we chose epoxy activation method to couple polysaccharide or a swellable organic polymer. In detail, 2-(2-Aminoethoxy)ethanol (AEE) was coupled to carboxyl-functionalized SAM using peptide coupling reagents (N-hydroxysuccinimide/N-Ethyl-N'-(3-dimethylaminopropyl)-carbodiimide (EDC/NHS)), and the terminal hydroxyl groups were further reacted with epichlorohydrin to produce epoxy-functionalized surfaces. These were subsequently reacted with hydroxyl moieties of polysaccharide or organic polymer. Subsequently, the polysaccharide chains were carboxylated through treatment with bromoacetic acid more than one time. The resultant material offered for further functionalization with biomolecules.

Rather than using single-component for preparing the SAM in conventional methods, "mixed" SAMs were used in the present invention, which provides various functional groups and branching structures to decrease the steric hindrance of interfacial reaction that, in turn, is useful for studying the biomolecular interaction analysis.

In addition, the facile surface plasmon resonance senses through specific biorecognizable gold substrates in combination with dextran using 2-(2-Aminoethoxy)ethanol (AEE) as a crosslinking agent, not gold nanoparticles as reported. As reported, dextran-treated surface was normally reacted with bromoacetic acid only one time. In our experiments, multiple bromoacetic acid reactions were employed in order to improve the carboxylated degree of dextran surface. Therefore, linking layer on the surface of a gold-film glass chip of the present invention significantly decreases the steric hindrance of interfacial reaction that, in turn, is useful for ligands immobilization.

Step Two: Immobilization of Representative Antibodies and Antigens on the Surface of the Linking Layer:
A dextran coated sensor chip was used in this invention. The surface of the chip matrix was first activated by injection of a suitable activating agent (such as EDC/NHS or EDC/sulfo-NHS); afterwards the activating agent was washed out and the ligand solution (representative antibodies and antigens in 10 mM acetate buffer) was injected. After coupling, the remaining active groups in the matrix were deactivated by injection of a suitable agent (such as ethanolamine solution), then the non-covalently bound ligand was washed out by a high ionic strength medium.

For most covalent immobilization methods, electrostatic preconcentration of the ligand in the surface matrix was achieved with 10 mM acetate buffer at a suitable pH (range from 3.5 to 5.5). In our experiments, representative antibodies and antigens were prepared in 10 mM acetate buffer with suitable pH at concentrations of 10-100 µg/ml.

For instance, the surface of a sensor chip was activated by EDC/NHS. The ligands (representative antibodies and antigens) in the 10 mM acetate buffer with suitable pH were spotted onto sensor chip using a microarray printing device. 1 M ethanolamine hydrochloride (pH 8.5) was used to deactivate excess reactive esters and to remove non-covalently bound ligand. Printed arrays were incubated in a humid atmosphere for 1 h and stored dry at 4° C. prior to use.

An important consideration for reproducibility is the ability to control the amount of representative antibodies and antigens spotted on the matrix. Ideally, identical amount of representative antibodies and antigens should be immobilized in the same area. Therefore, the use of reproducible amount of representative antibodies and antigens is a critical step to ensure accurate results, especially in high-density array systems. Spotted technologies for reproducible delivery of microarrays of biological samples are preferred.

There are two ligand-coupling ways:

1). Direct Coupling

Amine coupling introduces N-hydroxysuccinimide esters into the surface matrix by modification of the carboxymethyl groups with a mixture of N-hydroxysuccinimide (NHS) and N-ethyl-N'-(dimethylaminopropyl)-carbodiimide (EDC). These esters then react spontaneously with amines and other nucleophilic groups on the ligand to form covalent links. Amine coupling is the most generally applicable coupling chemistry, which is recommended as the first choice for most applications.

For most chemical coupling methods, preconcentration of a ligand on the surface matrix is important for efficient immobilization of macromolecules. This preconcentration can be accomplished by electrostatic attraction between negative charges on the surface matrix (carboxymethyl dextran) and positive charges on the ligand at pH values below the ligand pI, and allows efficient immobilization from relatively dilute ligand solutions. Electrostatic preconcentration is less significant for low molecular weight ligands.

Several important notes for the direct coupling are described as follows:

HBS-EP (pH 7.4) was first recommended. PBS (pH7.4) could be used as well.

The optimal pH for ligand immobilization is critically affected by the pH and ionic strength of the coupling buffer. The optimal condition for immobilization of thyroid hormones related antibodies or antigens were 10 mM acetate buffer at pH 5.0.

EDC/NHS (0.2 M N-ethyl-N'-(dimethylaminopropyl) carbodiimide/0.05 M N-hydroxysuccinimide) was injected to activate the surface.

The ligand solution was printed to the activated sensor chip surface.

1 Methanolamine hydrochloride (pH 8.5) was used to deactivate unreacted NHS-esters. The deactivation process also removed any remaining electrostatically bound ligand.

2) Indirect Coupling

Most macromolecules contain many groups that can participate in the amine coupling reaction, and immobilization is usually easy. There are, however, situations where other coupling methods may be preferable:

Ligands where the active site includes particularly reactive amino or other nucleophilic groups may lose biological activity on immobilization In certain situations, the multiplicity of amine coupling sites may be a disadvantage. The average number of attachment points for proteins to the matrix is normally low.

Several important notes for the indirect coupling are described as follows:

(1) HBS-EP (pH 7.4) was first recommended. PBS (pH7.4) could be used as well.

(2) NHS/EDC was injected to activate the sensor chip surface.

(3) 20 µg/ml of streptavidin in 10 mM acetate buffer at pH 5.0 was injected.

(4) 1 Methanolamine hydrochloride (pH 8.5) was injected to deactivate excess reactive esters and to remove non-covalently bound streptavidin.

(5) 10 µg/ml of biotinylated protein in HBS-EP (pH 7.4) was injected.

Step Three: Testing a Sample:

1. Preparation of the Serum Sample to Reduce Unwanted Binding

Unwanted binding may cause binding of analyte to non-specific sites on the surface, or binding of non-analyte molecules in the sample to the surface or the ligand. It is preferred to prepare the serum sample in order to obtain the best results.

One or more steps can be done for the serum preparation illustrated as follows:

(1) Inclusion of a surface-active agent, such as Surfactant P20 or Tween, in buffers and samples could help to reduce binding to non-specific sites, but could not guarantee that all binding would be biospecific.

(2) The use of physiological (0.15 M) salt concentrations could reduce non-specific electrostatic effects in most cases.

(3) Addition of zwitterions, such as taurine or betaine, could also help to reduce non-specific electrostatic adsorption.

(4) Addition of carboxymethyl dextran at approximate 1 mg/ml to the sample could reduce non-specific binding to the dextran matrix by competition effects.

(5) Addition of other monoclonal antibody at approximate 10 ug/l~10 ug/ml to a sample could amplify the signal.

(6) The serum sample could be diluted 2-10 fold by using 1-10% of BSA, 5-50% of Bovine Calf Sera, 10-50% of mouse serum or 10-50% of rabbit serum.

2. Sample Testing

To quantitatively analyze the levels of thyroid hormones and related antibodies in a serum sample, relevant antibodies and antigens were immobilized on the surface of the linking layer at predetermined concentrations, which allowed antibodies and antigens to react with various concentrations of representative thyroid hormones and related antibodies, respectively, in the serum.

Subsequently, the antibody-antigen reaction was detected with SPR system according to the standard operation procedure. Known concentrations of thyroid hormones and related antibodies in the serum and the relative resonance units (RU) of SPR were used to establish the standard curves. In comparison with standard curves, the concentrations of thyroid hormones and related antibodies in a serum sample to be tested are measured and quantified.

For comparison purposes, the same serum sample was checked for the same thyroid hormones and related antibodies as detected with SPR technology by using an ELISA method. The presence of different concentrations of thyroid hormones and related antibodies in a serum sample detected by SPR technology was consistent with those detected by ELISA methods.

In summary, as illustrated from the above detailed description and examples, the present invention demonstrates that the concentrations of different thyroid hormones and related antibodies in a serum sample were positively related to the RU. In addition, the present invention also provides a more efficient formula to make the dextran coated sensor chip for improved immobilization of thyroid hormones and related antibodies. The present invention demonstrates that SPR technology can be used to reliably detect thyroid hormones and related antibodies coated on the linking layer and the antibody-antigen reactions and the concentrations of different thyroid hormones and related antibodies in a serum sample measured by SPR system were consistent with those as detected with ELISA method.

It is to be understood that the above-described embodiments are only illustrative of application of the principles of the present invention. Numerous modifications and alternative embodiments can be derived without departing from the spirit and scope of the present invention and the appended claims are intended to cover such modifications and arrangements. Thus, while the present invention has been shown in the drawings and fully described above with particularity and detail in connection with what is presently deemed to be the most practical and preferred embodiment(s) of the invention, it will be apparent to those of ordinary skill in the art that numerous modifications can be made without departing from the principles and concepts of the invention as set forth in the claims.

We claim:

1. A SPR biosensor chip for detecting thyroid hormone related antibodies or antigens in a serum sample to evaluate thyroid functions and to diagnose thyroid diseases, prepared by forming a linking layer on the surface of a metal film on a glass chip and immobilizing of one or more thyroid hormones related antibodies or antigens on the surface of the linking layer, wherein said metal film is treated with dextran using 2-(2-Aminoethoxy)ethanol (AEE) as a crosslinking agent and multiple bromoacetic acid reactions.

2. The SPR biosensor chip according to claim 1, wherein the linking layer is prepared by preparing a mixed SAM of long-chain alkanethiols which can bind with biomolecules through its suitable reactive groups on one side and react with said gold film through a gold-complexing thiol on the other side, modifying and activating the mixed SAMs.

3. The SPR biosensor chip according to claim 2, wherein said mixed SAMs is prepared by one of the following: (1) coadsorption from solutions containing mixtures of alkanethiols (HS(CH2)nR+HS(CH2)nR'), (2) adsorption of asymmetric dialkyl disulfides (R(CH2)mS—S(CH2)nR'), and (3) adsorption of asymmetric dialkylsulfides (R(CH2)mS(CH2)nR'), wherein n and m are the number of methylene units which is an integer from 3 to 21 and R represents the end group of the alkyl chain (—CH3, —OH, —COOH, NH2) active for covalently binding ligands or biocompatible substance.

4. The SPR biosensor chip according to claim 2, wherein said modifying and activating the mixed SAMs is accomplished by an epoxy activation method to couple a polysaccharide or a swellable organic polymer comprising coupling 2-(2-Aminoethoxy)ethanol (AEE) to carboxyl-functionalized SAM using peptide coupling reagents (N-hydroxysuccinimide/N-Ethyl-N'-(3-dimethylaminopropyl)-carbodiimide (EDC/NHS)), and reacting with epichlorohydrin to produce epoxy-functionalized surfaces, which subsequently being reacted with hydroxyl moieties of the polysaccharide or organic polymer, the resulting polysaccharide chains are subsequently being carboxylated through treatment with bromoacetic acid multiple times.

5. The SPR biosensor chip according to claim 1, wherein said thyroid hormone related antibodies is a member selected from the group consisting of the antibodies to TSH, T3, T4, FT3 and FT4.

6. The SPR biosensor chip according to claim 1, wherein said thyroid hormone related antigen is a member selected from the group consisting of antigens of anti-TG and anti-TP.

7. The SPR biosensor chip according to claim 1, wherein said metal is copper, silver, aluminum or gold.

8. A method for detecting thyroid hormone related antibodies or antigens in a serum sample to evaluate thyroid functions and to diagnose thyroid diseases, comprising the steps of:
   1) preparing a surface plasmon resonance (SPR) system comprising:
      a) the SPR biosensor chip according to claim 1;
      b) a spectrophotometric means for receiving a first signal and a second signal from said surface, said second signal being received at a time after binding of said antibodies or antigens on said surface; and
      c) means for calculating and comparing properties of said first received signal and said second received signal to determine the presence of said thyroid related antibodies or antigens;
   2) contacting a serum sample to be tested with said biosensor surface and spectrophotometrically receiving said first signal and said second signal; and
   3) calculating and comparing differences to signals received from a standard curve of serum containing said thyroid related antibodies or antigens to determine the presence and quantity of said thyroid related antibodies or antigens which can be used to evaluate thyroid functions and to diagnose thyroid diseases.

9. The method according to claim 8, wherein the linking layer is prepared by preparing a mixed SAM of long-chain alkanethiols which can bind with biomolecules through its suitable reactive groups on one side and react with said gold film through a gold-complexing thiol on the other side, modifying and activating the mixed SAMs.

10. The method according to claim 9, wherein said mixed SAMs is prepared by one of the following: (1) coadsorption from solutions containing mixtures of alkanethiols (HS(CH$_2$)$_n$R+HS(CH$_2$)$_n$R'), (2) adsorption of asymmetric dialkyl disulfides (R(CH$_2$)$_m$S—S(CH$_2$)$_n$R'), and (3) adsorption of asymmetric dialkylsulfides (R(CH$_2$)$_m$S(CH$_2$)$_n$R'), wherein n and m are the number of methylene units which is an integer from 3 to 21 and R represents the end group of the alkyl chain (—CH$_3$, —OH, —COOH, NH$_2$) active for covalently binding ligands or biocompatible substance.

11. The method according to claim 9, wherein said modifying and activating the mixed SAMs is accomplished by an epoxy activation method to couple a polysaccharide or a swellable organic polymer comprising coupling 2-(2-Aminoethoxy)ethanol (AEE) to carboxyl-functionalized SAM using peptide coupling reagents (N-hydroxysuccinimide/N-Ethyl-N'-(3-dimethylaminopropyl)-carbodiimide (EDC/NHS)), and reacting with epichlorohydrin to produce epoxy-functionalized surfaces, which subsequently being reacted with hydroxyl moieties of the polysaccharide or organic polymer, the resulting polysaccharide chains are subsequently being carboxylated through treatment with bromoacetic acid multiple times.

12. The method according to claim 8, wherein said thyroid hormone related antibodies is a member selected from the group consisting of the antibodies to TSH, $T_3$, $T_4$, $FT_3$ and $FT_4$.

13. The method according to claim 8, wherein said thyroid hormone related antigen is a member selected from the group consisting of antigens of anti-TG and anti-TP.

14. The method according to claim 8, wherein said metal is copper, silver, aluminum or gold.

* * * * *